United States Patent [19]

Sipos

[11] Patent Number: 4,459,281
[45] Date of Patent: Jul. 10, 1984

[54] ANTICARIES COMPOSITIONS

[75] Inventor: Tibor Sipos, Lebanon, N.J.

[73] Assignee: Johnson & Johnson Products Inc., New Brunswick, N.J.

[21] Appl. No.: 442,698

[22] Filed: Nov. 18, 1982

[51] Int. Cl.³ .......................... A61K 7/16; A61K 7/18
[52] U.S. Cl. ........................................ 424/52; 424/49
[58] Field of Search .................................... 424/49–58

[56] References Cited

U.S. PATENT DOCUMENTS

| | | | |
|---|---|---|---|
| 4,243,658 | 1/1981 | Chang | 424/49 |
| 4,304,766 | 12/1981 | Chang | 424/52 |
| 4,307,077 | 12/1981 | Buck | 424/56 |
| 4,307,078 | 12/1981 | Buck | 424/56 |
| 4,314,991 | 2/1982 | Sipos | 424/56 |
| 4,360,512 | 11/1982 | Vidra | 424/56 |
| 4,360,513 | 11/1982 | Buck | 424/56 |
| 4,360,514 | 11/1982 | Buck | 424/56 |
| 4,360,515 | 11/1982 | Buck | 424/56 |
| 4,361,547 | 11/1982 | Sipos et al. | 424/56 |
| 4,362,712 | 12/1982 | Buck | 424/49 |
| 4,364,972 | 12/1982 | Sipos et al. | 424/56 |

OTHER PUBLICATIONS

A.D.A. Accepted Dental Therapeutics 38th Ed. Sep. 1979 American Dental Assn. Chicago, Ill. pp. 316–338 "Fluoride Compounds".

*Primary Examiner*—Shep K. Rose
*Attorney, Agent, or Firm*—Steven P. Berman

[57] ABSTRACT

Compositions providing improved protection against dental caries consisting of a pharmaceutically acceptable fluoride compound and a pharmaceutically acceptable alkyl phenoxy or oxydibenzene sulfonate in a suitable vehicle are described.

6 Claims, No Drawings

ANTICARIES COMPOSITIONS

BACKGROUND OF THE INVENTION

The present invention relates to compositions for preventing dental caries. More particularly, it relates to fluoride-containing compositions that have enhanced activity in preventing dental caries.

The use of soluble fluoride salts, such as stannous fluoride and sodium fluoride, to reduce the incidence of dental caries in the general population is a well-known and ongoing endeavor. The administration of these fluoride compounds takes many forms, including the fluoridation of drinking water, professional treatment by dentists and incorporation in oral hygiene compositions such as dentifrices and mouthrinses.

Notwithstanding the widespread acceptance of such compositions, there is an ongoing search for more effective compositions and, therefore, there is a need to enhance the fluoride activity of various fluoride compounds by the addition of other compounds. In copending U.S. patent application Ser. No. 303,284, filed Sept. 17, 1981 now U.S. Pat. No. 4,396,599, there is suggested the use of various vinc salts to enhance the activity off fluoride compounds.

One of the objects of the present invention is to provide improved compositions for preventing dental caries.

Another object of this invention is to provide anticaries compositions comprising one or more anticaries compounds in combination with a compound which enhances the anticaries activity of said anticaries compounds.

These and other objects of the invention will become apparent from the foregoing description.

SUMMARY OF THE INVENTION

In accordance with the present invention, there are provided compositions useful in preventing dental caries comprising (a) at least one fluoride salt and (b) a specific alkyl phenoxy or alkyl oxydibenzene sulfonate salt.

The enhancing effect on the anticaries properties of the compositions of the present invention is most notable when the fluoride salt is employed with an alkyl phenoxy or oxydibenzene sulfonate salt within specific concentrations and the compositions of the invention can be employed in various oral hygiene products.

DETAILED DESCRIPTION OF THE INVENTION

It has now been discovered that the rate of development of dental caries, as characterized by proximal, smooth surface, pit and fissure caries, can be prevented or substantially retarded by the daily application to the teeth of a composition comprising a pharmaceutically acceptable oral hygiene vehicle containing an effective concentration to prevent or inhibit dental caries of a pharmaceutically acceptable fluoride salt and a pharmaceutically acceptable alkyl phenoxy or oxydibenzene sulfonate salt.

Typical pharmaceutically acceptable fluoride compounds that are suitable for use in the compositions of this invention include sodium fluoride, potassium fluoride, lithium fluoride, aluminum fluoride, zinc fluoride, stannous fluoride, sodium monofluorophosphate, acidulated phosphate fluoride, ammonium fluoride, ammonium bifluoride and amine fluoride.

The alkyl phenoxy and alkyl oxydibenzene sulfonate salts found useful in accordance with the present invention are selected from the group consisting of bis(alkylphenoxy)alkane sulfonate salts of the structure (A),

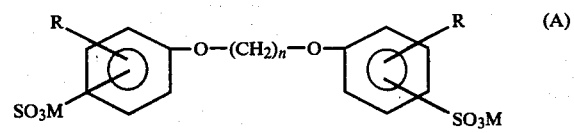

Monoalkyldiphenyloxide monosulfonate salts of the structure (B),

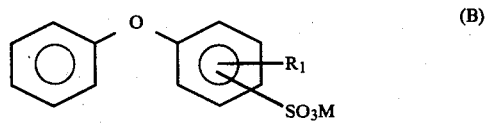

dialkyldiphenyloxide monosulfonate salts of structure (C),

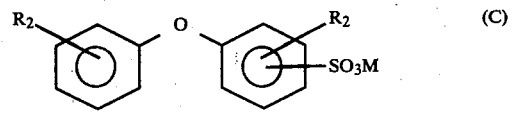

monoalkyldiphenyloxide disulfonate salts of the structure (D),

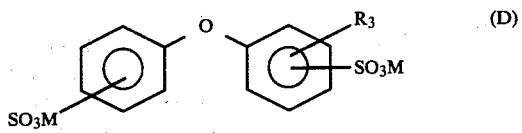

dialkyldiphenyloxide disulfonate salts of the structure (E),

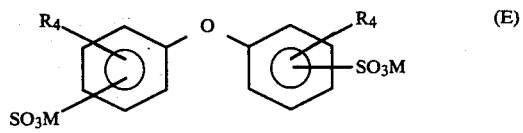

monoalkyloxydibenzene monosulfonate salts of the structure (F),

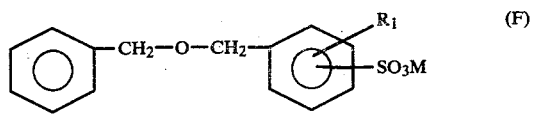

dialkyloxydibenzene monosulfonate salts of structure (G),

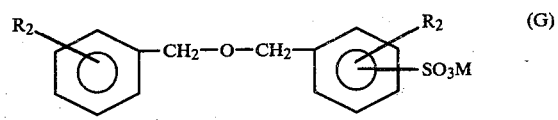

monoalkyloxydibenzene disulfonate salts of the structure (H),

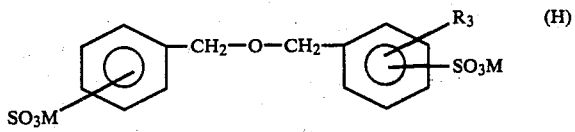

dialkyloxydibenzene disulfonate salts of structure (I),

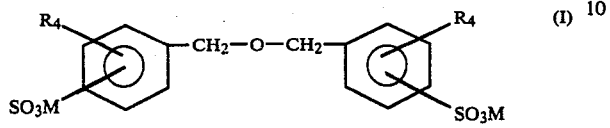

wherein R is a linear or branched chain alkyl containing from 10 to 20 carbon atoms; $R_1$, $R_2$, $R_3$ and $R_4$ are linear or branched chain alkyl containing from 8 to 20 carbon atoms, n is an integer from 2 to 4; and M is selected from the group consisting of hydrogen, lithium, sodium potassium, calcium, magnesium, zinc, aluminum, copper, ammonium and the substituted ammonium ions derived from pharmaceutically acceptable organic amines.

The synthesis of the bis(alkylphenoxy)alkane sulfonate salts of structure A is essentially identical to that reported by M. J. Rosen, M. Baum, and F. Kasher [Journal of the American Oil Chemists' Society, Volume 53, pp. 742-745] for the synthesis of the corresponding symmetrical disodium sulfonates which contain no alkyl substituents on the phenyl rings.

The compounds shown in structures (B)-(I) can be prepared in the same general manner as described above for the compounds of structure A and also according to the teachings in U.S. Pat. No. 2,990,375 which teachings are incorporated herein by reference. Some of the alkyl and dialkyl diphenyloxide and oxydibenzene monosulfonate and disulfonate salts are available from Dow Chemical Company, Midland, Mich. under the general tradename of Dowfax. Some of the specific Dowfax compounds useful include Dowfax 2AI and Dowfax XD 8390.

In connection with the above compositions, the fluoride ion concentration should be from about 0.005 to 2.00% by weight of the total composition, preferably from about 0.01 to 1.00% The concentration of the alkyl phenoxy and alkyl oxydibenzene sulfonate salts should be at least 0.0001% by weight of the total composition, preferably from about 0.01 to 5.00% and most preferably from about 0.05 to 3.00%. In concentrate formulations, the sulfonated materials may have a concentration as high as 80% by weight of the total composition.

Suitable pharmaceutically acceptable oral hygiene vehicles, that may be used alone or in any compatible combination, include glycerol, water, ethanol, polyethylene glycol, propylene glycol and sorbitol. Alternatively, any pharmaceutically acceptable vehicle which is compatible with the sulfonated material and fluoride salts used may be employed.

The compositions of this invention may be in the form of a mouthrinse, dentifrice, gel, powder, solution, varnish, lozenge, chewing gum, slow release device or concentrate to be diluted or other form suitable for oral application. Any pharmaceutically acceptable materials, such as those ordinarily used in such oral compositions, that are compatible may be employed in the compositions of this invention.

In accordance with the present invention, the compositions are applied to the teeth with an appliance, e.g., toothbrush, swab, mechanical cleansing devices, impregnated dental floss or the like, by gently brushing the teeth at least once daily, more preferably twice daily.

Specific embodiments of the anticaries compositions prepared in accordance with the present invention are illustrated by the following representative examples. It will be understood, however, that the invention is not confined to the specific limitations set forth in the individual examples, but rather to the scope of the appended claims.

EXAMPLE I

A gel dentifrice is prepared as follows: the Pluronic F-127 surface active agent is dissolved in 50 ml. of deionized water with continuous stirring at 70° C. The sodium salt of a sulfonated 1,4-bis(dodecylphenoxy)butane is then added with stirring until dissolved. The resultant solution is then cooled to 50° C. and the sodium fluoride, glycerol, sorbitol, sodium benzoate, sweetener, flavoring, dye and silicone dioxide are individually added. The pH of the solution is then adjusted to 5.5 to 6.0 with 1.0N HCl or 1.0N NaOH as required and deionized water is added to bring the total weight to 100 g. The solution is permitted to gel overnight at 15° C.

The resulting gel dentifrice has the following composition:

|  | % w/w |
|---|---|
| sodium fluoride | 0.22 |
| sodium salt of a sulfonated 1,4-bis-(dodecylphenoxy)butane | 1.00 |
| silicon dioxide | 1.00 |
| Pluronic F-127 (Wyandotte Chemicals Corporation's tradename for a nonionic surface active agent prepared by the addition of ethylene oxide to polypropylene glycol) | 18.00 |
| sweetener | 0.80 |
| sodium benzoate | 0.30 |
| glycerol | 10.00 |
| sorbitol solution, 70% | 2.00 |
| flavoring | 0.80 |
| dye (0.5% aq. soln.) | 0.70 |
| deionized water | q.s. to 100 |

EXAMPLE II

An abrasive paste dentifrice is prepared as follows: the sodium fluoride, sodium benzoate, sweetener, Pluronic F87 and Dowfax XD 8390 are dissolved in 25 ml. of water at 50° C. with continuous stirring. In separate vessels, the xanthan gum is mixed with the glycerol and the Natrosol 250H is mixed with the sorbitol and then each of these mixtures is added to the solution. The Zeothix 265, titanium dioxide, and hydrous silica gel are then individually added to the solution with stirring. The pH of the solution is then adjusted to 5.0 to 6.0 with 1.0N HCl or 1.0N NaOH as required and the flavoring is then added as well as enough deionized water to bring the solution to 100 g. The resultant product is mixed and placed in containers and permitted to stand at 20° C. overnight.

The resulting abrasive paste dentifrice has the following composition:

| | % w/w |
|---|---|
| sodium fluoride | 0.22 |
| Dowfax XD 8390 (Dow Chemical Company's tradename for the disodium 4-hexadecylated oxydibenzene sulfonate) | 1.00 |
| sodium benzoate | 0.20 |
| sweetener | 0.50 |
| titanium dioxide | 0.50 |
| flavoring | 1.00 |
| glycerol | 10.00 |
| sorbitol soln. 70% | 12.00 |
| hydrous silica gel | 15.00 |
| Zeothix 265 | 9.00 |
| Natrosol 250H (Hercules Inc. tradename for nonionic water soluble cellulose ether) | 1.00 |
| xanthan gum | 1.00 |
| Pluronic F87 (Wyandotte Chemical Corporation's tradename for a nonionic surface active agent prepared by the addition of ethylene oxide to polypropylene glycol) | 3.00 |
| deionized water | q.s. to 100 |

EXAMPLE III

A mouthrinse solution is prepared as follows: the flavoring is dissolved in ethanol in a suitable stainless steel vessel. The Pluronic F-108, water, glycerol, sorbitol, sweetener, Dowfax 2A1 and sodium fluoride are individually added with continuous stirring. The pH is adjusted to 5.5 to 6.0 with 1.0N HCl as required and the entire solution is strained through a 400 mesh stainless steel screen.

This resulting mouthrinse has the following composition:

| | % w/w |
|---|---|
| sodium fluoride | 0.05 |
| Dowfax 2Al (Dow Chemical Company's tradename for the sodium salt of a dodecyl diphenoxy disulfonate) | 0.02 |
| ethanol, USP | 7.0 |
| Pluronic F108 (Wyandotte Chemical Corporation's tradename for a nonionic surface active agent prepared by the addition of ethylene oxide to polypropylene glycol) | 2.00 |
| glycerol | 10.00 |
| sorbitol soln. 70% | 10.00 |
| sweetener | 0.20 |
| flavoring | 0.20 |
| deionized water | q.s. to 100 |

EXAMPLE IV

An in vitro assay technique is utilized to demonstrate the enhancing properties of the sulfonated polymeric material on fluoride ion activity. This technique is based on the titrametric measurement of organic acids produced from sucrose by the cariogenic bacterium *S. mutans*.

A fresh cell suspension of *Streptococcus mutans* 6715, grown in Trypticase Soy Broth for 16–18 hrs. at 35° C., centrifuged and the cells then resuspended in buffer containing dithiothreitol is used in the assay system. The cell suspension is stored under anaerobic conditions at 4° C. until used. The assay utilizes a pH-stat and the reaction is carried out under a nitrogen atmosphere at 37° C. The production of acid is monitored with the automatic addition of 0.005N potassium hydroxide solution. The cells are initially activated with glucose at pH 7.5. After the exhaustion of glucose, the pH of the reaction mixture is manually dropped to 5.5 with 0.01N HCl. Sucrose is added and after 4 minutes of acid production, the test compound is added. The rate of acid production is recorded as ml of potassium hydroxide consumed per minute to maintain a pH of 5.5. Antiacidogenic activity is reported as that amount of compound which reduces the acid production by a given percent as compared to a control containing no test compound. The higher the percent reduction of acid production of a composition containing the sulfonated materials and fluoride ion compared to a composition containing the sulfonated material alone, the better the anticaries activity of such a composition.

The following table shows the results when various compounds falling within the scope of this invention are tested:

| | | % reduction of acid product | | |
|---|---|---|---|---|
| Compound | Concentration | Compound Alone | Fluoride Alone | Compound plus fluoride ion |
| sodium salt of a sulfonated 1,4-bis-(dodecylphenoxy) butane | 0.001 | 23 | 20 | 67 |
| | 0.002 | 65 | 20 | 93 |
| Dowfax 2Al | 0.001 | 27 | 20 | 70 |
| | 0.002 | 64 | 20 | 100 |
| Dowfax XD 8390 | 0.0005 | 27 | 20 | 63 |
| | 0.001 | 41 | 20 | 100 |

In addition to the preferred embodiments described herein, other embodiments, arrangements, and variations within the spirit of the invention and the scope of the appended claims will occur to those skilled in the art.

What is claimed is:

1. In a composition for preventing dental caries consisting essentially of a pharmaceutically acceptable oral hygiene vehicle containing an effective concentration to prevent caries of at least one pharmaceutically acceptable fluoride salt; the improvement which consists of including therewith ion activating enhancing amount of a pharmaceutically acceptable alkyl phenoxy or alkyloxydibenzene sulfonate salt selected from the group consisting of:

bis(alkylphenoxy)alkane sulfonate salts of the structure (A),

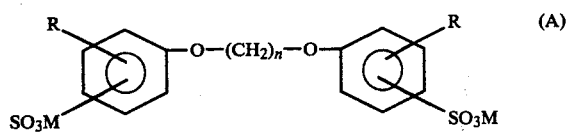

monoalkyldiphenyloxide monsulfonate salts of the structure (B),

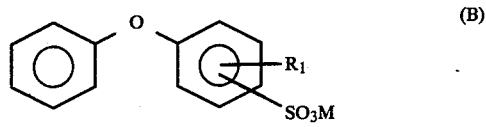

dialkyldiphenyloxide monsulfonate salts of structure (C), monoalkyldiphenyloxide disulfonate salts of the structure (D),

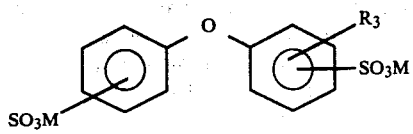

dialkyldiphenyloxide disulfonate salts of the structure (E),

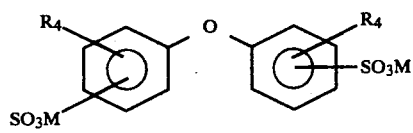

monoalkyloxydibenzene monosulfonate salts of the structure (F),

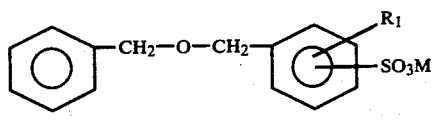

dialkyloxydibenzene monosulfonate salts of the structure (G),

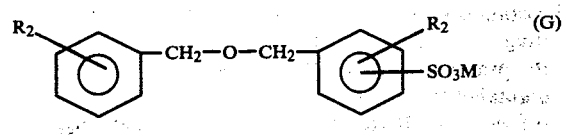

monoalkyloxydibenzene disulfonate salts of the structure (H),

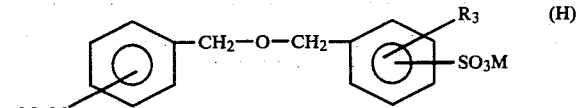

dialkyloxydibenzene disulfonate salts of structure (I),

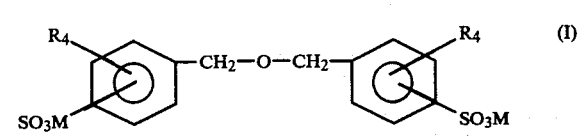

wherein R is a linear or branched chain alkyl containing from 10 to 20 carbon atoms; $R_1$, $R_2$, $R_3$ and $R_4$ are linear or branched chain alkyl containing from 8 to 20 carbon atoms, n is an integer from 2 to 4; and M is selected from the group consisting of hydrogen, lithium, sodium, potassium, calcium, magnesium, zinc, aluminum, copper, ammonium and the substituted ammonium ions derived from pharmaceutically acceptable organic amines.

2. The composition of claim 1 wherein the sulfonated material is a salt of a sulfonated 1,4-bis(dodecylphenoxy)butane.

3. The composition of claim 1 wherein the sulfonated material is a salt of a dodecyl diphenoxy disulfonate.

4. The composition of claim 1 wherein said fluoride salt is selected from the group consisting of sodium fluoride, potassium fluoride, lithium fluoride, aluminum fluoride, zinc fluoride, stannous fluoride, sodium monofluorophosphate, acidulated phosphate fluoride, ammonium fluoride, ammonium bifluoride and amine fluoride.

5. The composition of claim 1 wherein the fluoride ion is present in a concentration of from about 0.005 to 2.00% by weight of the total composition.

6. The composition of claim 1 wherein the sulfonated material is present in an amount of from about 0.0001 to 80.00% by weight of the total composition.

* * * * *